United States Patent
Schütz

(10) Patent No.: US 7,822,255 B2
(45) Date of Patent: Oct. 26, 2010

(54) METHOD AND APPARATUS FOR GENERATION OF AN X-RAY IMAGE

(75) Inventor: Oliver Schütz, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1039 days.

(21) Appl. No.: 11/518,479

(22) Filed: Sep. 8, 2006

(65) Prior Publication Data

US 2007/0058772 A1  Mar. 15, 2007

(30) Foreign Application Priority Data

Sep. 9, 2005   (DE) .................. 10 2005 043 051

(51) Int. Cl.
*G06K 9/00* (2006.01)
(52) U.S. Cl. ...................... 382/132; 382/173
(58) Field of Classification Search ............ None
See application file for complete search history.

(56) References Cited

U.S. PATENT DOCUMENTS

| 5,268,967 | A | * | 12/1993 | Jang et al. ................ 382/6 |
|---|---|---|---|---|
| 5,617,461 | A | | 4/1997 | Schreiner .................. 378/98.5 |
| 5,982,916 | A | * | 11/1999 | Kuhn ........................ 382/132 |
| 6,650,729 | B2 | | 11/2003 | Braess et al. ............... 378/108 |
| 6,775,399 | B1 | * | 8/2004 | Jiang ......................... 382/128 |
| 7,046,836 | B2 | * | 5/2006 | Shinbata .................... 382/132 |
| 7,627,154 | B2 | * | 12/2009 | Luo et al. ................... 382/128 |
| 2004/0125921 | A1 | | 7/2004 | Allouche et al. ........... 378/207 |
| 2004/0228443 | A1 | * | 11/2004 | Bohm et al. ................. 378/97 |
| 2005/0018893 | A1 | * | 1/2005 | Wang et al. ................ 382/132 |

FOREIGN PATENT DOCUMENTS

| DE | 197 42 152 A1 | 3/1999 |
|---|---|---|
| DE | 198 47 219 A1 | 5/1999 |

* cited by examiner

*Primary Examiner*—Andrew W Johns
(74) *Attorney, Agent, or Firm*—Schiff Hardin LLP

(57) ABSTRACT

In a method and an apparatus for generation of an x-ray image of an examination subject, a subject image region exclusively reproducing the examination subject is identified in the image field of a first, complete x-ray image. A grayscale value range is identified in an intermediate image encompassing the entire image field and derived from the first x-ray image by digital image processing; and all image points whose grayscale value in the intermediate image lie within this grayscale value range are associated with the subject image region.

16 Claims, 8 Drawing Sheets

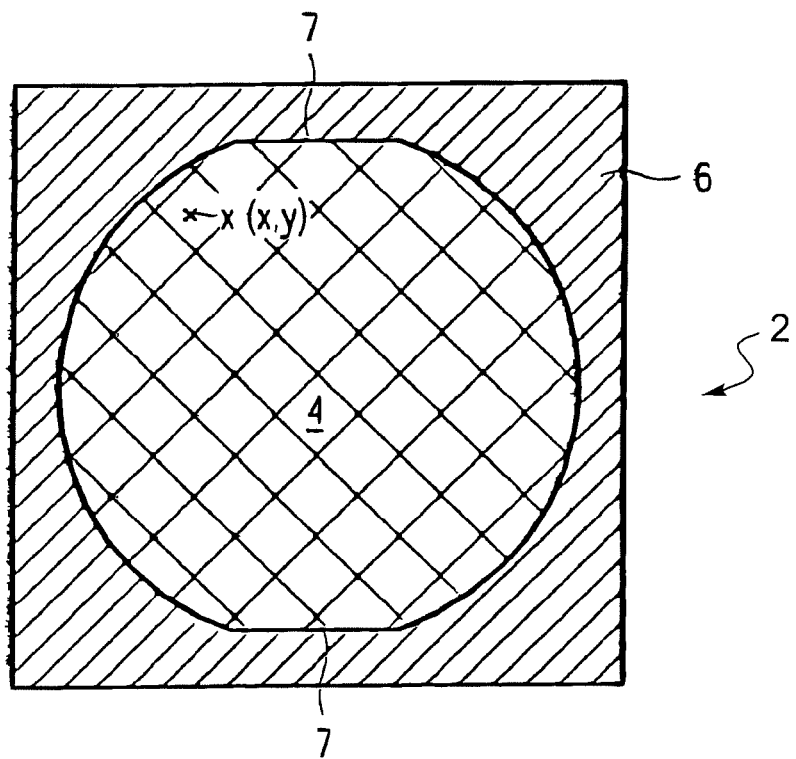
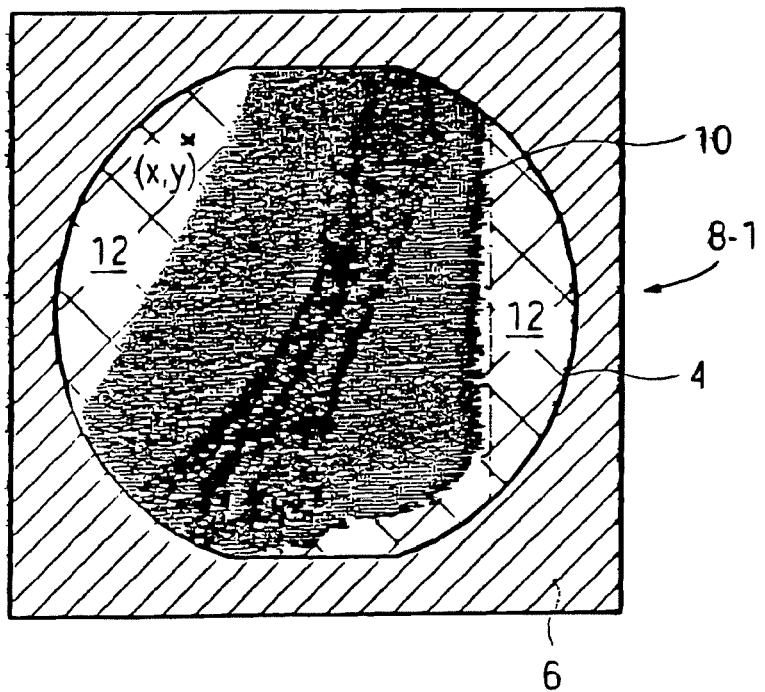

METHOD AND APPARATUS FOR GENERATION OF AN X-RAY IMAGE

BACKGROUND OF THE INVENTION

1. Field of the Invention

The present invention concerns a method and an apparatus for generation of an x-ray image of an examination subject.

2. Description of the Prior Art

The diagnostic utilization capability of an x-ray image, meaning the ability to detect structures within the examination subject, is significantly influenced by two factors. These are apparatus-dependent acquisition parameters such as, for example, the anode/filter combination of the x-ray tube, and the correct exposure, and the manner with which the x-ray image is displayed on a reproduction medium.

For exposure or dose control, i.e. to control the x-ray dose required for an x-ray image, it is known (in particular in the implementation of diagnostic or therapeutic methods) to acquire a first, complete x-ray image with a dose estimated based on experiential values (which x-ray image is diagnostically usable), for example given the image support of an operative procedure in which it is necessary to generate a number of x-ray images of the examination subject in short time intervals. In a measurement field of this x-ray image that is situated in the central image region, the arithmetic average of the intensity or of the brightness is then calculated, for example. This average is compared with a stored desired value. By means of this comparison the dose for the acquisition of the next x-ray image is adjusted such that the real value of the intensity or brightness coincides optimally well with the desired value.

The measurement field used for the determination of the real value is static with regard to its position, shape and size, meaning that it is always the same in all exposures. Such a static measurement field, however, can lead to a reduced image quality in disadvantageous cases due to a non-optimal x-ray dose. One of the main causes for this is direct radiation incident in the measurement field. Direct radiation is x-rays that have not passed through the examination subject and thus are unattenuated. Due to this direct radiation the real value of the intensity averaged over the measurement field is raised. This leads to the situation that the x-ray dose for the following acquisition is reduced until the desired value is reached. The result is an underexposed x-ray image.

A cause for direct radiation in the measurement field can be, for example, a poor positioning of the examination subject during the imaging or the fact that the examination subject being examined is smaller than the actual, statically-defined measurement field.

For correct use of the dose control, in particular in mobile C-arm x-ray apparatuses, it is therefore necessary for the user (the doctor or medical-technical assisting personnel) to position the patient (i.e. the examination subject) such that optimally no direct radiation can strike the central measurement field. In other words; the central measurement field must be optimally completely covered by the patient. Experience shows, however, that such an ideal positioning of the patient is not always ensured or possible for the imaging. In order nevertheless to obtain qualitatively good x-ray images in such cases, in principle the possibility exists to deactivate the automatic dose controller and to manually control the acquisition parameters, but this does not represent a satisfactory solution in light of experience.

In addition to an optimal dose control, in the reproduction of x-ray images it is also desired that the image regions that are diagnostically relevant for the doctor be shown with optimal quality on the monitor or in the archiving as a hard copy (film, foil). This diagnostically-relevant image region is formed by the region of the image field in which the image of the subject (the patient) is located.

Optimal quality means that the grayscale values within the subject image region enable an optimally differentiated, high-contrast (and thus well recognizable and thus diagnostically usable) reproduction of structures within this subject image region. By contrast, the remaining image regions should be reproduced such that they do not distract the observer. A main problem in the reproduction of the x-ray images is the direct radiation regions that occur in the x-ray image with high brightness.

The image data that are present at the output of an x-ray receiver and already subjected to a pre-processing, meaning the measured intensity I of the x-ray radiation as a function of the image coordinate (x, y), normally exist with a resolution (for example 4096 intensity levels) that cannot be used in the reproduction medium, for example a monitor with 256 grey levels.

In order to achieve as optimal an image display as possible, these intensity values must be mapped to the grayscale values that can be displayed on the reproduction medium, the mapping occurring with suitable transformation rules (lookup characteristic lines or lookup tables). In other words: the grayscale values used for the image display are associated with the intensities belonging to the individual image points. In known x-ray apparatuses, the entire x-ray image is always evaluated for the determination of these greyscale values since in particular the presence or the position of direct radiation regions in the x-ray image is not known in advance. This has the result that the grayscale values in the subject image region are no longer displayed with the best possible contrast resolution of the monitor (i.e. no longer utilizing the maximum possible grayscale value or grey level with, for example, 256 grayscale value), but rather are displayed with few grayscale values since, in the transformation, the extreme values (diaphragm region and direct radiation region) of the intensities measured by the x-ray receiver significantly limit the grayscale value range remaining for the subject image region in the transformation.

Moreover, direct radiation regions present in the x-ray image can visually "overload" the observer. The contrast resolution capability of the eye is thereby reduced and fine contrast details in the subject image region are also not detectable when they are reproduced on a monitor. Moreover, such over-intensity is always uncomfortable and should be generally avoided for this reason.

The possibility does exist in principle to minimize the direct radiation regions using diaphragms (X-iris diaphragms or filter diaphragms). In practice, however, this possibility is frequently not used since a correct setting of the diaphragms is time-consuming, particularly in the acquisition of a number of x-ray exposures from different directions. Moreover, due to the complex geometric shape of the examination subject, such a setting of diaphragms preventing direct radiation regions is not possible in all cases without loss of diagnostic information.

SUMMARY OF THE INVENTION

An object of the invention is to provide a method for generation of an x-ray image of an examination subject with which the achievable image quality is improved. A further object of the invention is to provide an apparatus for implementation of such a method.

With regard to the method, the above object is achieved by a method wherein a subject image region exclusively reproducing the examination subject is identified in the image field of a first complete x-ray image, in which subject image region a grayscale value range of an intermediate image encompassing the entire image field and derived from the first x-ray image by digital image processing is identified. All image points (pixels) having grayscale values in the intermediate image lie within this grayscale value range are associated with the subject image region. Since such a grayscale value analysis is conducted not directly on the first x-ray image but rather on an x-ray image (subsequently designated as an intermediate image) processed by digital image processing, an identification of the actual subject image region that reproduces the examination subject is assured.

A calibration image is generated in the absence of an examination subject and stored in a preceding step. Using this calibration image a calibrated second x-ray image is calculated from the first x-ray image (from which second x-ray image the intermediate image is derived). Apparatus-conditional influences (for example a vignetting given the use of an x-ray image intensifier) thus can be largely eliminated.

In a preferred embodiment of the method, an edge-reduced x-ray image is used as the intermediate image, the edge-reduced x-ray image being generated by processing the first x-ray image or of the calibrated second x-ray image with an edge filter. Deletion of the edge regions determined in this manner in the first or calibrated second x-ray image then is undertaken. In this manner it is possible to separate the image points that are clearly associated with the subject image region from the remaining image points, since the image points in the transition zones formed by the subject edges no longer exhibit grayscale values that lie between the grayscale value of the subject image region and the grayscale value of a direct radiation region located next thereto. In other words, the grayscale value range formed by the subject image region is clearly separated from grayscale value ranges that are not associated with (do not belong to) the subject image region.

A grayscale value histogram of the intermediate image can be generated and the frequency zero is associated with all grayscale values whose frequency of occurrence in the grayscale value histogram falls below a predetermined first threshold. The computation outlay required for the image processing is thereby reduced.

In an embodiment of the method, starting from a maximum measured current greyscale value that is smaller than the maximum possible grayscale value in the grayscale value histogram of the intermediate image, a grayscale value occurring with the maximum frequency is identified in a first search interval adjoining this maximum current grayscale value. Starting from this grayscale value occurring with the maximum frequency, an analysis is made in a second search interval adjacent to this grayscale value and located below this grayscale value, as to whether the frequency of the grayscale values falls below a predetermined second threshold. The grayscale value at which this threshold is first under-run in the search for the direction of smaller grayscale values is identified as a first upper grayscale value of a first grayscale value range reproducing a first subject image region. This procedure assures detection of the grayscale value range of the subject image region when the available dynamic range in the first x-ray image is not exceeded.

As an alternative, i.e. in a situation in which the dynamic range is exceeded, starting from a maximum current grayscale value that is equal to the maximum possible grayscale value in a predetermined third search interval, whose upper limit value is formed by the maximum possible grayscale value, it is analyzed whether the frequency of the grayscale values falls below a predetermined second threshold. The grayscale value at which this threshold is first under-run in the search in the direction of smaller grayscale values is identified as a first upper grayscale value of a first grayscale value range reproducing a first subject image region.

In another embodiment of the method, starting from the first upper grayscale value of the subject image region a greyscale value is determined at which, in a search in the direction of smaller grayscale values, the second threshold is under-run, and this is identified as a second upper grayscale value of a second grayscale value range reproducing a second subject image region. In other words, up to those image points with the grayscale values of zero, all image points whose grayscale values or smaller than the second upper grayscale value are associated with the subject image region. The brightened regions at the border of the subject image region with the direct radiation region are thereby eliminated from the subject image region.

When an average grayscale value of the subject image region is determined and used to control the dose of a subsequent x-ray image to be acquired, a correct exposure of the x-ray image is ensured.

A representation optimized for the observer is enabled by using, for reproduction of an x-ray image, the image regions of the x-ray image whose grayscale values in the intermediate image lie outside of the grayscale value range of the subject image region, as virtual diaphragms in a uniform display.

A further improvement of the reproduction quality is achieved when the grayscale values for the image reproduction are determined exclusively from the grayscale value range of the subject image region.

The above object also is achieved in accordance with the present invention by an apparatus for generating an x-ray image that operates according to the above-described method, and all embodiments thereof.

DESCRIPTION OF THE DRAWINGS

FIG. 1 illustrates a blank or direct radiation image.

FIGS. 2a, 3a and 4a respective show a first x-ray image, a calibrated second x-ray image and an edge-reduced x-ray image.

DESCRIPTION OF THE PREFERRED EMBODIMENTS

Figure 2B:
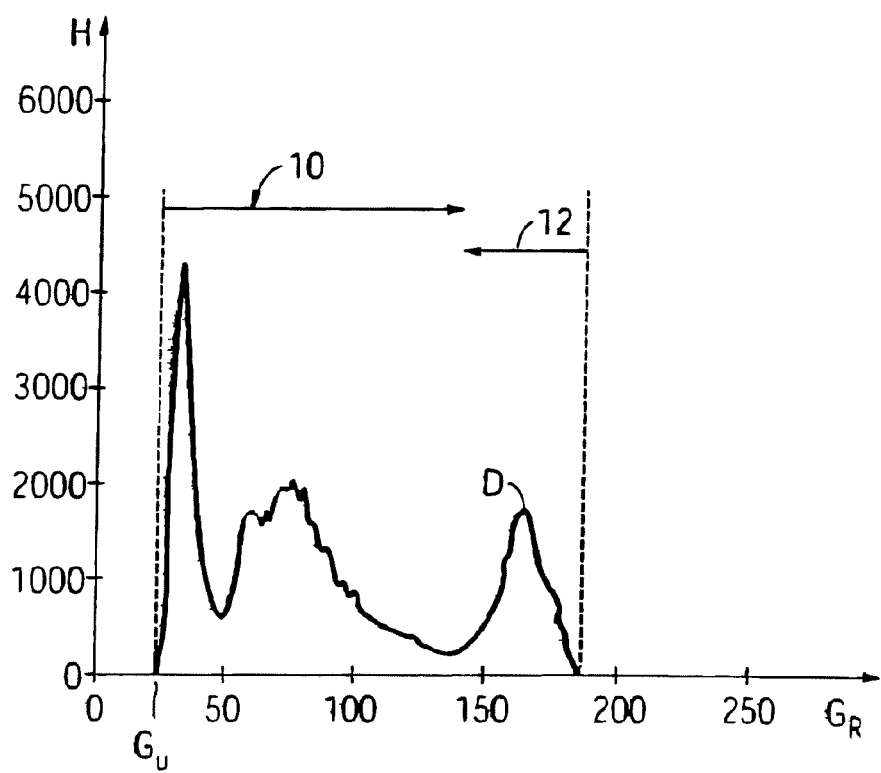
FIGS. 2b, 3b and 4b show grayscale value histograms respectively associated with FIGS. 2a, 3a, and 4a in which the frequency with which a greyscale value occurs in the x-ray image is plotted against the grayscale value.

As shown in FIG. 1, a blank or direct radiation image 2 is generated in a first step of the inventive method with a predetermined set of acquisition parameters in the absence of an examination subject. If an x-ray image intensifier is used as an x-ray detector, this direct radiation image 2 has an approximately circular, brightly exposed image field 4 that is surrounded by a border region 6 generated by a diaphragm (for example a static aperture, an X-iris diaphragm or a filter diaphragm) or by a mask used in digital image processing. This border region 6 is shown in FIG. 1 by hatching and is not taken into account in the following steps explained for determination of the measurement field. A grayscale value G(x, y) is associated with each image point (x, y) of the direct radiation image 2.

Moreover, in FIG. 1 the direct radiation image 2 is shown with a cross-hatching indicating that in practice the intensity of the direct radiation in the image field 4 is not constant and varies from apparatus to apparatus. The cause for this can be, for example, vignetting, meaning a darkening that increases toward the image border when an x-ray image intensifier is used as the x-ray receiver. The normally circular image of such an x-ray image receiver is bordered by diaphragms 7 in the example of FIG. 1. Further causes for inhomogeneities occurring in the direct radiation image 2 can be an inhomogeneity of the ray filter, an inhomogeneity of the x-ray radiation emitted by the x-ray source (Heel effect) or external interference sources.

The direct radiation image 2 can be additionally processed by digital image processing methods to reduce the image noise and to improve the image quality. The acquisition parameters for the direct radiation image 2 should be selected such that an optimally good signal/noise ratio is achieved and an excess irradiation occurs at no point in the image.

From the direct radiation image 2 generated in this manner, a calibration image is now generated by normalization of its grayscale values to the value range [0, 0 . . . 1, 0] (all grayscale values are divided by the maximum grayscale value), in which calibration image a normalized greyscale value $G_K(x, y)$ is associated with each image point (x, y). It can also be advantageous to assemble a number of direct radiation images 2 into an averaged calibration image. Furthermore, it can be advantageous to calculate the averaged calibration image from direct radiation images 2 that have been measured with at different spatial orientations of an x-ray C-arm, if an image intensifier detector is used as the x-ray receiver. A change of the orientation of the image intensifier detector leads to a slight image rotation and image shift since the image intensifier detector is influenced by the earth's magnetic field. These changes are thereby averaged out.

The generation of the calibration image can be implemented at the manufacturer's factory before the delivery of the x-ray system, and the calibration image is permanently stored in the x-ray system. Due to unavoidable aging effects, however, it can be appropriate to update the calibration from time to time, for example after one or two years.

In a second step, according to FIG. 2a, a first complete x-ray image 8-1 is now generated in the presence of an examination subject. In FIG. 2a it can be seen that this examination subject only occupies a subject image region 10 of the usable image field 4 situated within the masked border region 6, which subject image region 10 being smaller than the image field 4. Due to the small dimensions of the examination subject, direct radiation regions 12 that brighten the image field 4 are located in the image field 4 in addition to this subject image region 10. For example, given a dose control in which the measurement field significantly extends beyond the subject image region 10, these direct radiation regions 12 would lead to an under-exposure of the subject image region 10. Moreover, a static measurement field that is significantly smaller than the subject image region 10 and, for example, lies in the middle of the image field 4, would also not lead to a correct dose control since in this case a soft tissue surrounding the bone in the shown example would be overexposed.

Moreover, the direct radiation regions 12 that are present in the x-ray image 8-1 disturb the observer and subjectively reduce the detection capability of structures present in the subject image region 10. Due to the relatively bright direct radiation regions 12 that still exhibit the vignetting explained in FIG. 1, dynamic range inherently present for the image reproduction would also not be optimally used.

A grayscale value histogram of the x-ray image of in FIG. 2a is shown in FIG. 2b. Like the histograms shown in the following Figures, the histogram shown in FIG. 2a is smoothed (for example via a median filtering). From this grayscale value histogram it can be discerned that the x-ray image is not overexposed, since the existing dynamic range, meaning the grayscale value range available for the display of the x-ray image (256 grey levels from 0 to 255 given 8-bit image data) is not utilized. In this diagram the number or frequency of occurrence H of the image points is plotted dependent on the grayscale value $G_R$. The image points in the boundary region 6 have the grayscale value 0 so that a delta-shaped peak (not shown in FIG. 2a) occurs in the histogram. In FIG. 2 it can be seen that the grayscale values that are associated with the direct radiation region and are represented by the right peak D still cannot be sufficiently separated from the grayscale values that are present in the subject image region 10. In other words, an upper limit of the subject image region 10 beginning with a grayscale value of approximately 25 cannot be unambiguously established since the transition between subject image region 10 and direct radiation region 12 is blurred. The cause for this is that the distance covered by the x-rays through the examination subject (and thus also their (absorption) continuously decreases toward the subject edge, and the intensity thus increases.

Using the calibration image generated in a preceding step, a calibrated second x-ray image 8-2 is now computationally generated in which the grayscale value $G_R(x, y)$ of each image point (x, y) of the first x-ray image 8-1 is divided by the grayscale value $G_K$ of the appertaining image point (x, y) of the calibration image. The greyscale values $G_{Rk}$ of the calibrated x-ray image thus result via the relation $G_{RK}(x, y) = G_R(x, y)/G_K(x, y)$.

By means of calibration it is possible for the grayscale value of individual image points exceed the dynamic range (meaning that, given 8-bit image data, image points can receive a value greater than 255 through the calibration). All of these pixels can be reset to the maximum allowed grayscale value (given 8-bit image data to the maximum grayscale value 255) without disadvantages.

Figure 3A:
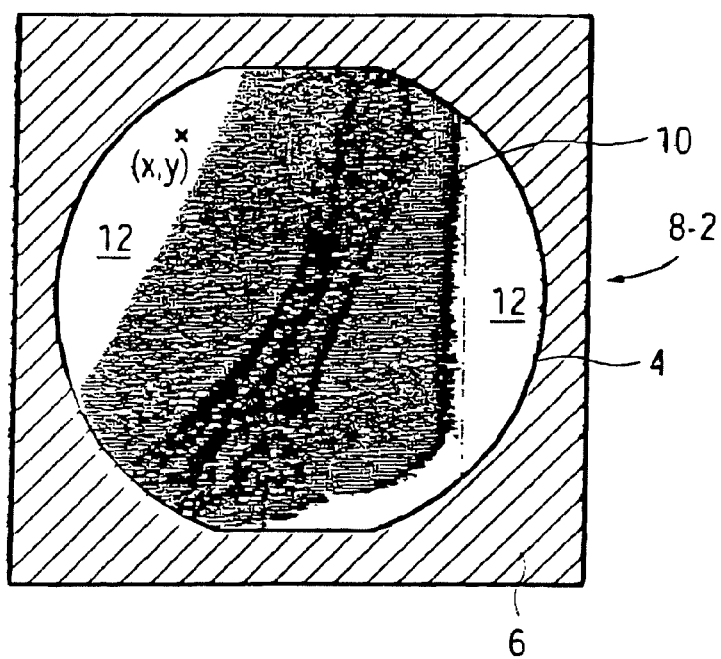

In this manner a calibrated second x-ray image 8-2 is generated as an intermediate image as is shown in FIG. 3a, and in which the direct radiation regions 12 are more homogeneous (i.e. with approximately constant grayscale value) as is illustrated in FIG. 3a by the absence of the cross-hatching.

Figure 3B:
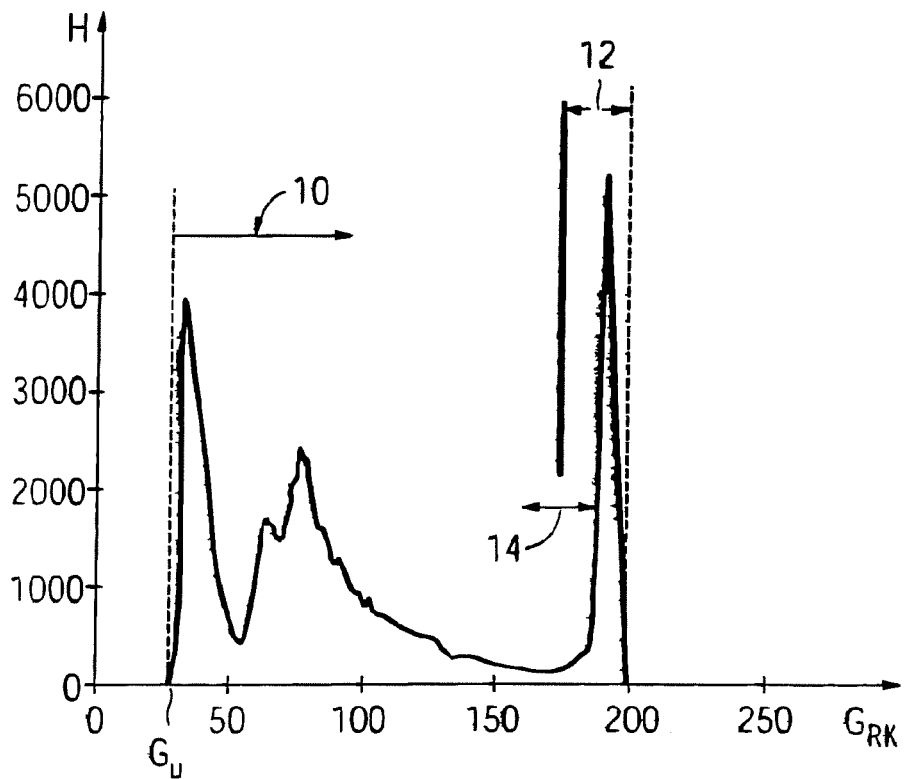

In the associated histogram according to FIG. 3b it is clearly recognizable that the direct radiation region 12 is already separated from the subject image region 10 after this image processing step. A comparison of FIG. 3b and 2b shows that the curve shape is also altered at lower grey levels by the calibration. Nevertheless, in this histogram an exact establishment of the boundary between the subject image region 10 and the direct radiation region 12 is still not unambiguously possible, as is illustrated by the double arrow 14.

In order to clearly emphasize an edge region 16 of the examination subject and to delimit it from the direct radiation region 12, in a next step the calibrated x-ray image 8-2 is subjected to an edge filtering in which, for example, an image known as a variance image is generated from the calibrated x-ray image 8-2. In this filter method a quantity (variance) that indicates how significantly the grayscale value varies in the surroundings is calculated for each image point (x, y). For a window size of 3×3 image points (x, y) in the exemplary embodiment, the quadratic deviation of the grayscale values is determined from an average in this window. This is the variance of the image point in the window mean. All image points (x, y) are then deleted in the calibrated x-ray image 8-2, meaning that 0 is associated with the grayscale value that exhibits a variance that exceeds a defined threshold. All image points are thus deleted that lie on an edge. The threshold can be dependent on a local grayscale value $G_{RK}(x, y)$ of the calibrated patient image 8-2. For example, the threshold $S(x, y)$ can be provided by the relation $S(x, y)=\alpha G_{RK}(x, y)$, with $\alpha$ being a constant that can be empirically determined and, among other things, is dependent on the image size and on the contrast resolution of the imaging x-ray system.

Instead of such a variance filtering, other edge filters with which the image edges can be identified are also suitable.

Figure 4A:
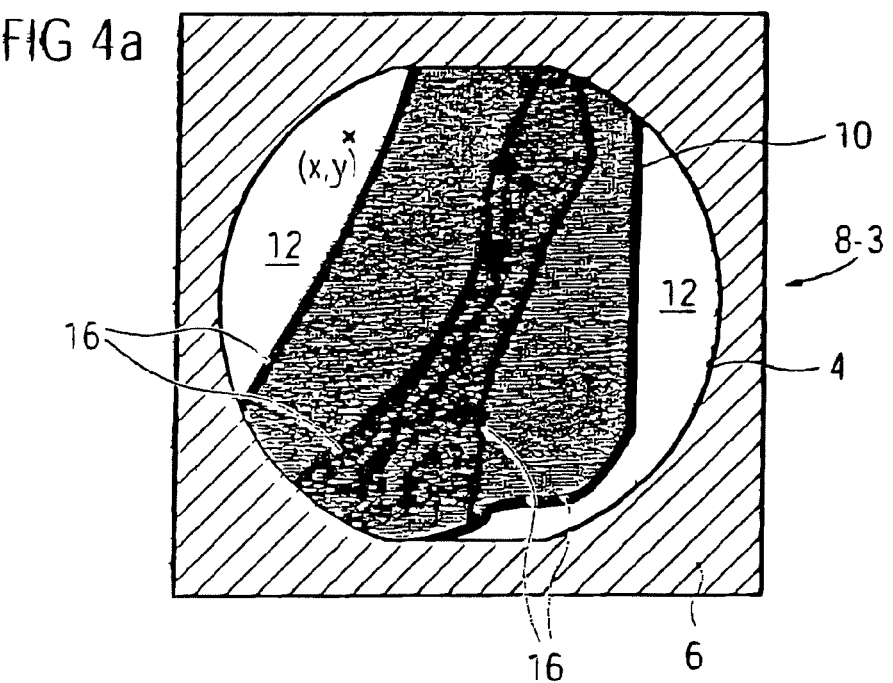

A calibrated, edge-reduced x-ray image 8-3 arising in this manner is now shown in FIG. 4a. In this calibrated, edge-reduced x-ray image 8-3 the existing edge regions 16 are now clearly recognizable as black lines. These are located both on the border of structures within the subject image region 10 and on the border between subject image region 10 and direct radiation region 12. This calibrated, edge-reduced x-ray image 8-3 now serves as an intermediate image in which a grayscale value range associated with the subject image region 10 is identified.

Figure 4B:
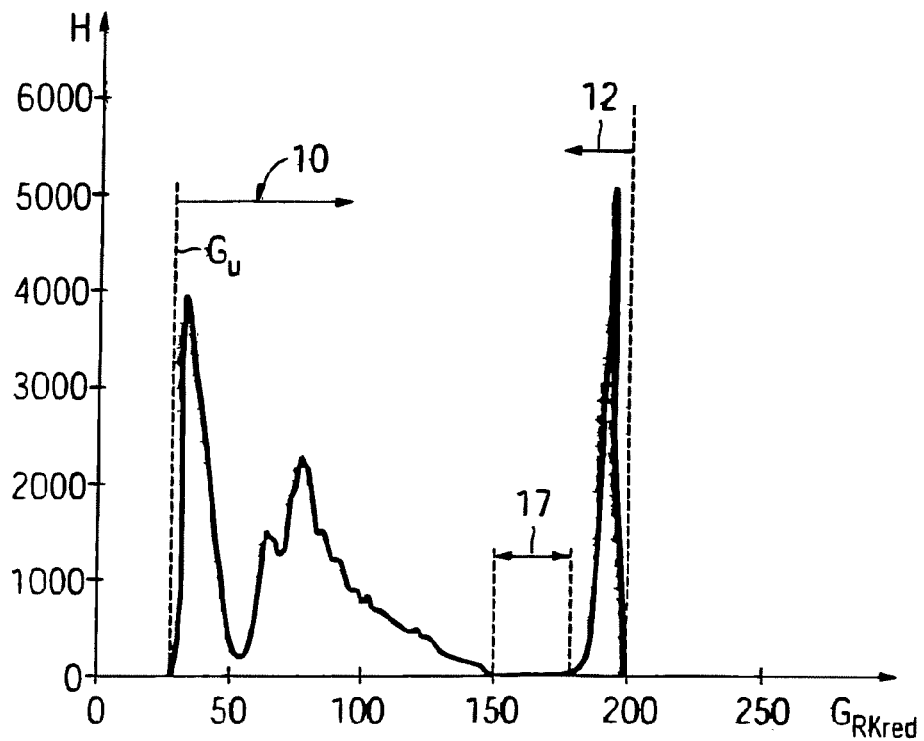

FIG. 4b now shows the grayscale value histogram of the edge-reduced x-ray image 8-3, in which it can be seen that the grayscale values associated with the direct radiation region 12 are significantly delineated from the grayscale values associated with the subject image region 10. In other words: a clearly developed intermediate space 17 arises between the grayscale values of the direct radiation region 12 and the grayscale values of the subject image region 10. Moreover, all grayscale values $G_{RKred}$ in the histogram that seldom occur can be deleted. In other words: a grayscale value $G_{RKred}(x, y)$ is associated with each image point (x, y), which grayscale value $G_{RKred}(x, y)$ occurs at a lower frequency than a first threshold $H_1$ in the grayscale value histogram of the calibrated, edge-reduced x-ray image 8-3; in this case the grayscale value 0 is associated with this grayscale value $G_{RKred}(x, y)$. The threshold $H_1$ must be determined by suitable methods for each system type. It depends on the image size (number of the image points) and on the physical image quality. The greater the noise proportion in the image, the higher that the threshold $H_1$ must be set. The grayscale value at which (starting from the grayscale value G=0) the first threshold $H_1$ is exceeded first is established as a lower grayscale value $G_U$ of the subject image region 10.

Using the grayscale value histogram generated in this manner, the direct radiation regions or, respectively, the subject image region is now segmented, i.e. established. Various scenarios I-VI thereby result in the x-ray image 8-3, which scenarios I=VI can be classified in two clusters A and B and are reproduced in the following table.

| Scenario | Description | Cluster |
|---|---|---|
| I | No direct radiation present in the x-ray image and dynamic range is not exceeded | A |
| II | No direct radiation present in the x-ray image and dynamic range is partially exceeded | B |
| III | Direct radiation present in the x-ray image, this has not exceeded the dynamic range | A |
| IV | Direct radiation present in the x-ray image, this has partially exceeded the dynamic range | B |
| V | Direct radiation present in the x-ray image, this has completely exceeded the dynamic range | B |
| VI | Direct radiation present in the x-ray image, even the subject has partially exceeded the dynamic range | B |

Cluster A is formed by calibrated, edge-reduced x-ray images in which no image point exceeds or less than $H_1$ image points exceed, the existing dynamic range 0 to 255 with its grayscale value. In other words, given an image with 8-bit contrast resolution the maximum existing grayscale value is less than 255, independent of whether direct radiation is present or not in the calibrated, edge-reduced x-ray image.

Scenarios II, IV, V and VI are combined in cluster B, the common feature of which is that the dynamic range is exceeded in a calibrated, edge-reduced x-ray image. In other words: given a calibrated, edge-reduced x-ray image with 8-bit contrast resolution, there is at least one image point, or there are at least $H_1$ image points, that has or have a grayscale value of at least 255.

Figure 5:
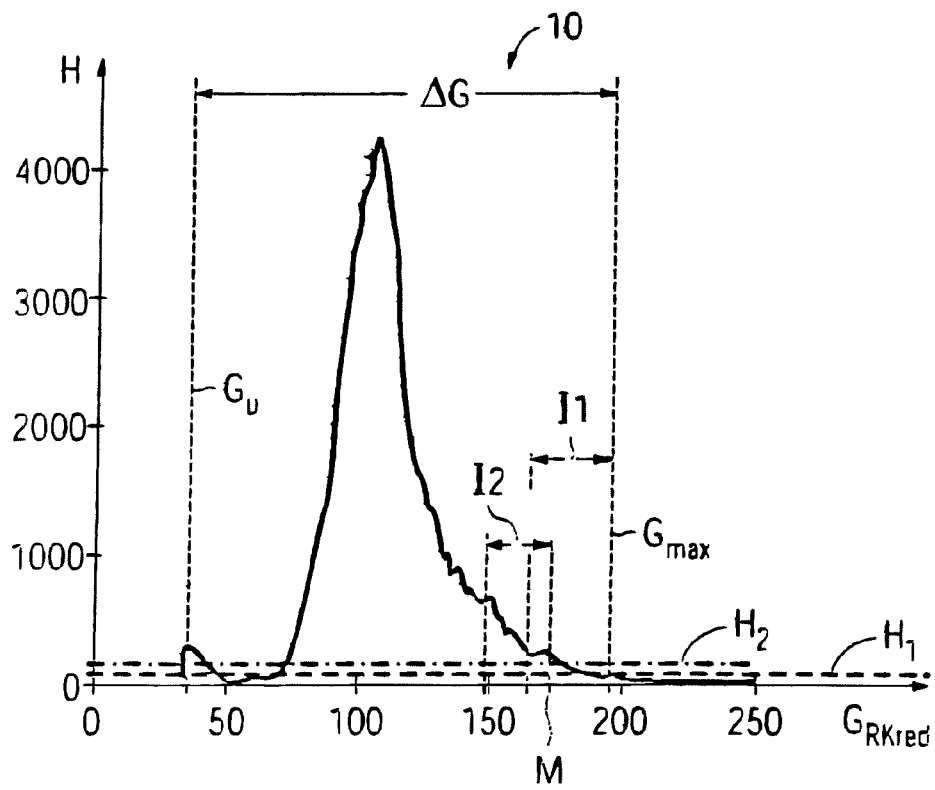
FIG. 5 is a grayscale value histogram of an edge-reduced x-ray image in which direct radiation does not occur, nor is the dynamic range exceeded.

FIG. 5 now shows a grayscale value histogram of a calibrated, edge-reduced x-ray image in which no direct radiation occurs, which is different than in the x-ray images 8-1, 8-2 or 8-3 respectively shown in FIGS. 2a, 3a and 4a. The absence of a direct radiation region, or the fact that the subject image region fills the entire image field is now recognized by, in a first step, the maximum current grayscale value $G_{max}$ in the histogram that occurs with a frequency $H>H_1$ being determined. Starting (i.e. in the direction of lower grayscale values) from this grayscale value $G_{max}$, within a predetermined first search interval I1 lying below (given smaller values) this maximum current grayscale value $G_{max}$ and bordering this (the search interval I1 encompassing, for example, 1/10 of the dynamic range, i.e. approximately 25 grey levels given a resolution of 8 bits), the grayscale value M is determined that occurs most frequently in this first search interval I1. Starting from this maximum (i.e. likewise in the direction of lower grayscale values), the grayscale value at which the histogram first falls below a predetermined second threshold $H_2$ is sought in a second search interval I2 that is attached to the search interval I1 or (as in the shown example) partially overlaps it. This second search interval I2 is located below the grayscale value M that is simultaneously the upper limit of this second search interval. In FIG. 5 it is now recognizable that all grayscale values that are greater than, for instance, 190 in the grayscale value histogram only occur with a frequency that lies below the first threshold $H_1$. If these grayscale values are deleted as explained in the preceding, the search for the most frequent grayscale value M thus begins given a grayscale value of, for instance, 190. Such a maximum is now established, for instance, at a grayscale value G=170. Starting from this most frequent grayscale value M, the grayscale value at which the second threshold $H_2$ is under-run is now sought in the second search interval I2. It can be seen from FIG. 5 that such a grayscale value does not exist. This is an indication that no direct radiation occurs in the x-ray image (cluster A, scenario I). In this case the grayscale value range $\Delta G$ to be associated with the subject image region 10 extends from $G_U$ to $G_{max}$.

Figure 6:
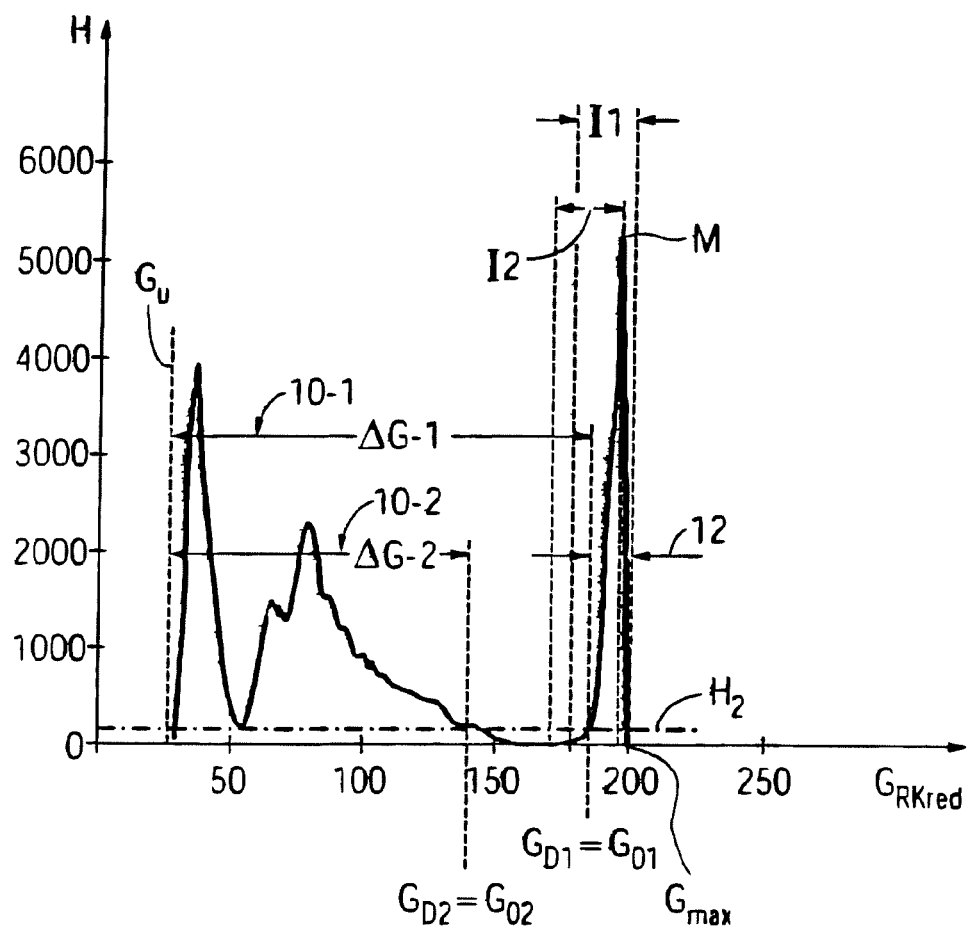
FIG. 6 is a grayscale value histogram of an edge-reduced x-ray image in which direct radiation occurs, but the dynamic range is not exceeded.

A different situation results according to FIG. 6 in the grayscale value histogram of the calibrated, edge-reduced x-ray image 8-3 as it is shown in FIG. 4b (cluster A, scenario III). Starting from the maximum grayscale value $G_{max}$ that lies at approximately 200 in the Fig., there in FIG. 6 a maximum M at a greyscale value of approximately 195 is identified in the first search interval I1. Starting from this maximum M, in the search interval I2 the grayscale value is sought at which the second threshold $H_2$ is first under-run given a search in the direction of smaller grayscale values. In the example of FIG. 6 this is a grayscale value of approximately 185 that is identified as a first lower grayscale value $G_{D1}$ (first lower direct radiation limit) of a first direct radiation region 12-1. This is simultaneously the first upper grayscale value $G_{O1}$ of a first subject image region 10-1 that thus is represented by image points that exhibit a grayscale value $G(x, y)$ that is smaller than the grayscale value $G_{D1}$ at the lower limit of the first direct radiation region 12-1. Lower greyscale value $G_U$ and first upper grayscale value $G_{O1}$ establish a first grayscale value range $\Delta G\text{-}1$ of the first subject image region 10-1.

Due to the small tissue thickness at the edge, all image points at the edge of the examination subject exhibit very high grayscale values since the x-ray radiation is less or even barely attenuated in this region. The real brightness value calculated from the subject region is therewith raised by the light edge points. In order to reduce the influence of the border zone of the subject image region, it is appropriate to set a second lower greyscale value $G_{D2}$ of a second direct radiation region 12-2 at a grayscale value position at which the histogram again exceeds the second threshold $H_2$, i.e. given a search starting from the first lower grayscale value $G_{D1}$ in the direction of smaller grayscale values. This second lower grayscale value $G_{D2}$ of the direct radiation is simultaneously the second upper grayscale value $G_{O2}$ of a second, limited subject image region 10-2. In other words: the grayscale value range associated with the boundary of the examination subject and situated between the first lower grayscale value $G_{D1}$ and the second lower grayscale value $G_{D2}$ is associated with the second direct radiation region 12-2. The second subject image region 10-2 is formed by the second grayscale value range $\Delta G\text{-}2$.

Figure 7:
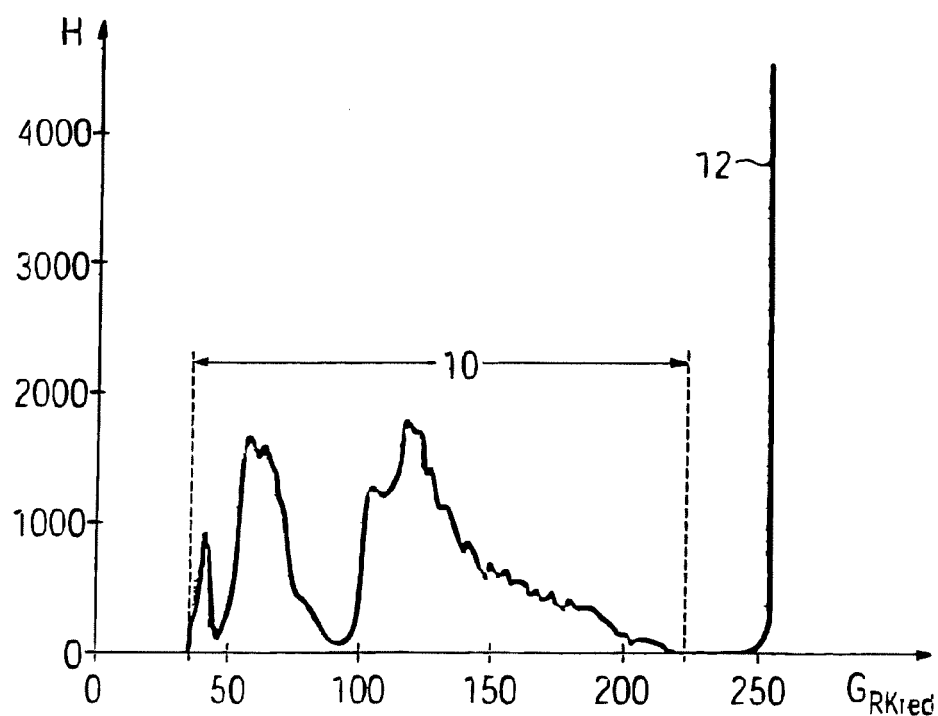
FIG. 7 shows an edge-reduced x-ray image in which direct radiation occurs and the dynamic range is exceeded.

The histogram of the calibrated, edge-reduced x-ray image according to FIG. 7 is for the situation wherein the dynamic range is exceeded due the occurrence of direct radiation given correct exposure of the subject image region 10. This is apparent because the subject image region 10 and the direct radiation region 12 are separated by a clearly developed grayscale value zone (cluster B, scenario V) and the direct radiation exhibits almost solely the grayscale value 255.

Figure 8:
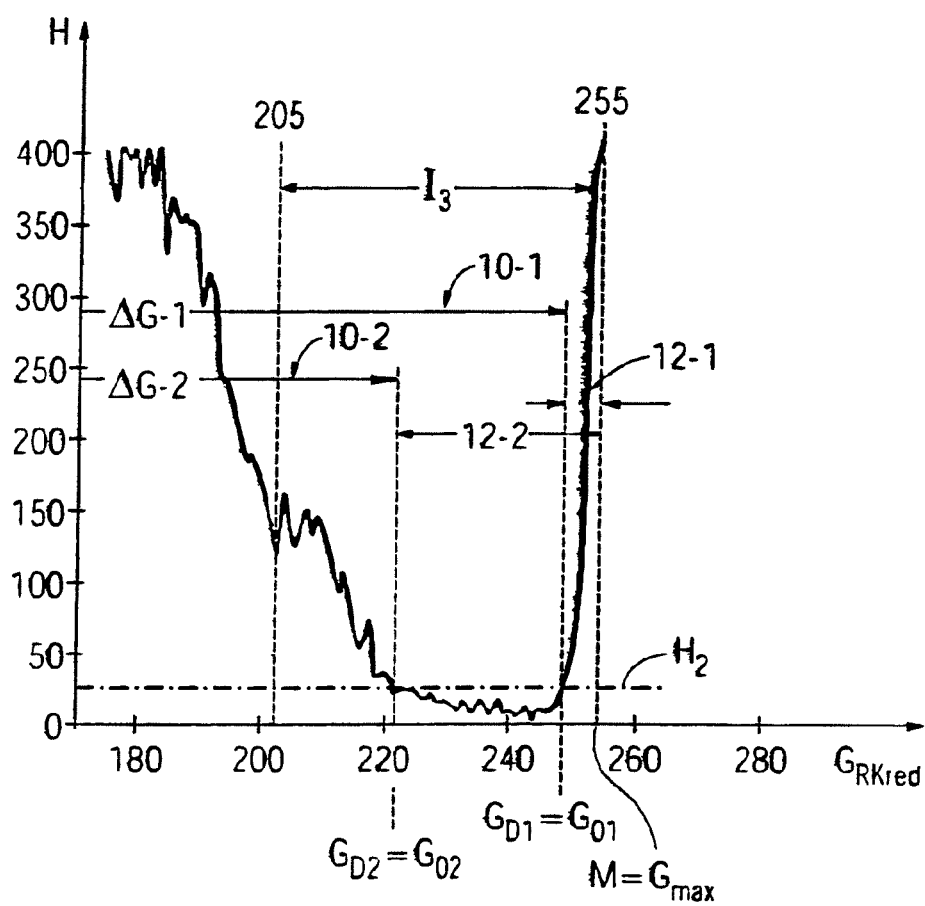
FIG. 8 is an enlarged section from the grayscale value histogram of FIG. 7.

The upper grayscale value range of FIG. 7 is shown enlarged in FIG. 8. In FIG. 8 it can be seen that the dynamic range is exceeded by the direct radiation in the manner that the upper limit of the dynamic range simultaneously corresponds to the maximum grayscale value $G_{max}$ and the maximum M of the direct radiation in the grayscale value histogram. In this case, starting from the upper limit of the dynamic range a third search interval I3 is established that encompasses approximately 20% of the dynamic range (i.e. approximately 50 grayscale levels) in the example.

As explained in connection with FIG. 6, starting from this maximum the grayscale value is determined as a first lower grayscale value $G_{D1}$ of the direct radiation region 12 in which the frequency with which image points $(x, y)$ with this grayscale value occur falls below a predetermined second threshold $H_2$ for the first time. The boundary of the second subject image region 10-2 now devoid of the subject edge, is formed by a second lower or upper grayscale value $G_{D2}$ or $G_{O2}$ in which the second threshold $H_2$ is exceeded again. In FIG. 6 this is the case given a grayscale value of approximately 220.

Figure 9:
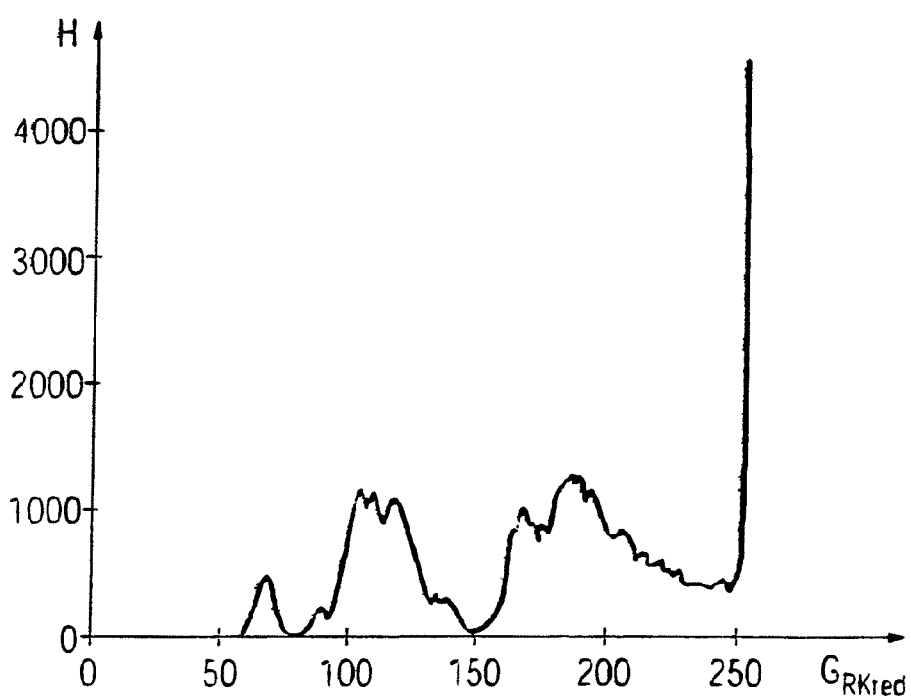
FIG. 9 is a grayscale value histogram of an edge-reduced x-ray image generated from an overdosed primary x-ray image.
Figure 10:
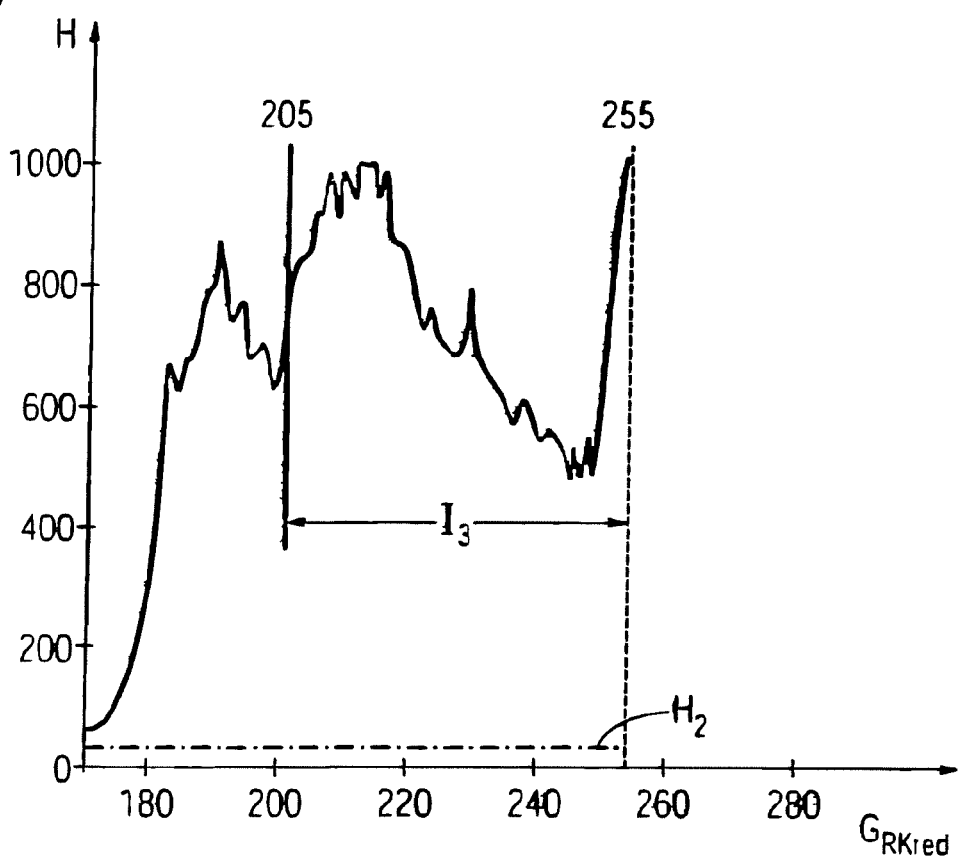
FIG. 10 is an the enlarged representation of a sub-range of the greyscale value histogram of FIG. 9.

FIG. 9 shows a grayscale value histogram of an edge-reduced x-ray image in which the examination subject is excessively irradiated, i.e. has been acquired with too high a dose (cluster B, scenario VI). As can be seen in the enlarged partial representation of FIG. 10, in this case the second threshold $H_2$ is not under-run in the search interval I3. In such a situation all image points with the maximum grayscale value (255) are classified as direct radiation. First and second upper grayscale values $G_{O1}$ and $G_{O2}$ coincide, and $G_{O1}=G_{O2}=254$.

Figure 11:
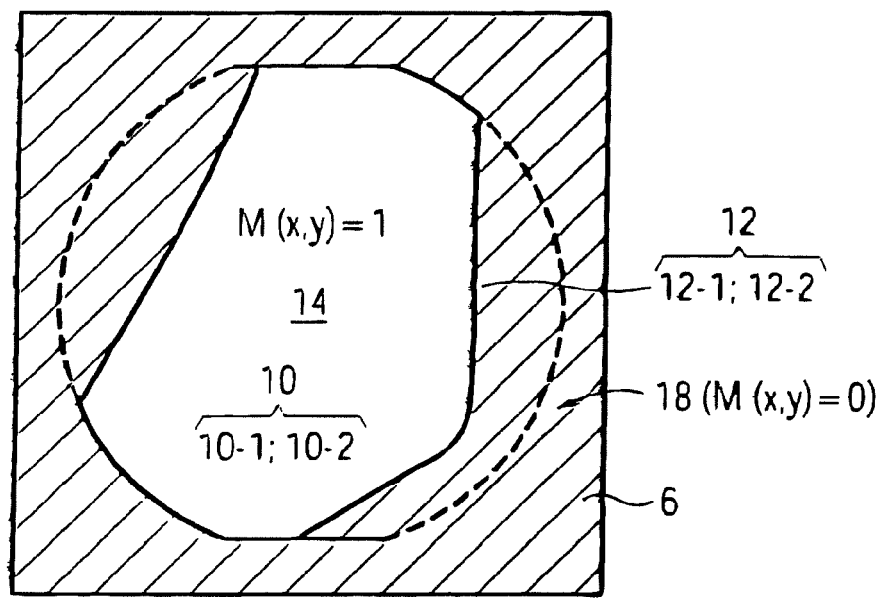
FIG. 11 is a subject mask encompassing only the subject image region.

As shown in FIG. 11, the grayscale value range established by the first and second upper greyscale values $G_{O1}$ or $G_{O2}$ of the first and second subject image region 10-1 and 10-2 are now used as a basis for the calculation of a subject mask in that all image points $(x, y)$ of the calibrated, edge-reduced x-ray image 8-2 that exhibit a grayscale value $G_{RKred}(x, y) > G_U$ and $G_{RKred}(x, y) < G_{O1}$ or $< G_{O2}$ receive the value 1 in the subject mask. The value 0 is associated with the remaining image points $(x, y)$ in the subject mask. In other words: a subject mask $M(x, y)$ is calculated for which the relation $M(x, y)=1$ applies for all image points $(x, y)$ with $G_U \leq G_{RKred}(x, y) < G_{O1}$ or $< G_2$ and $M(x, y)=0$ applies for all image points $(x, y)$ with other grayscale values.

The image region 18 defined by $M(x, y)=0$ then essentially encompasses the direct radiation region 12 (12-1, 12-2) and the diaphragm region 6.

The current bright real value for the dose control can be directly calculated from the histogram given the knowledge of the grayscale value range $(G_u, G_{O1} (G_{O2}))$ of the subject. This real brightness value is formed, for example, by the arithmetic mean of the greyscale values of the subject region.

The subject mask $M(x, y)$ can be used in order to optimize the reproduction of the x-ray image, in that (for example) all areas that lie outside of this subject mask $M(x, y)$ are rendered by a modified representation. Such a modified representation, for example, can mean that the subject mask $M(x, y)$ is superimposed on the x-ray image such that regions outside of the subject ($M(x, y)=0$) are shown in color or are darkened (virtual diaphragm).

The representation of the x-ray image, for example on a monitor, can be improved given the knowledge of the grayscale value range of the subject by the grayscale value range in the subject image region 10 being optimally mapped to the grayscale value range of, for example, the monitor.

In a modification of the procedure explained in the preceding in which a calibrated, edge-reduced x-ray image is used as an intermediate image for identification of the subject image region, in a simplified procedure it is also possible to directly use the first uncalibrated x-ray image, the calibrated x-ray image or an uncalibrated, edge-reduced x-ray image generated directly from the first x-ray image as an intermediate image.

Figure 12:
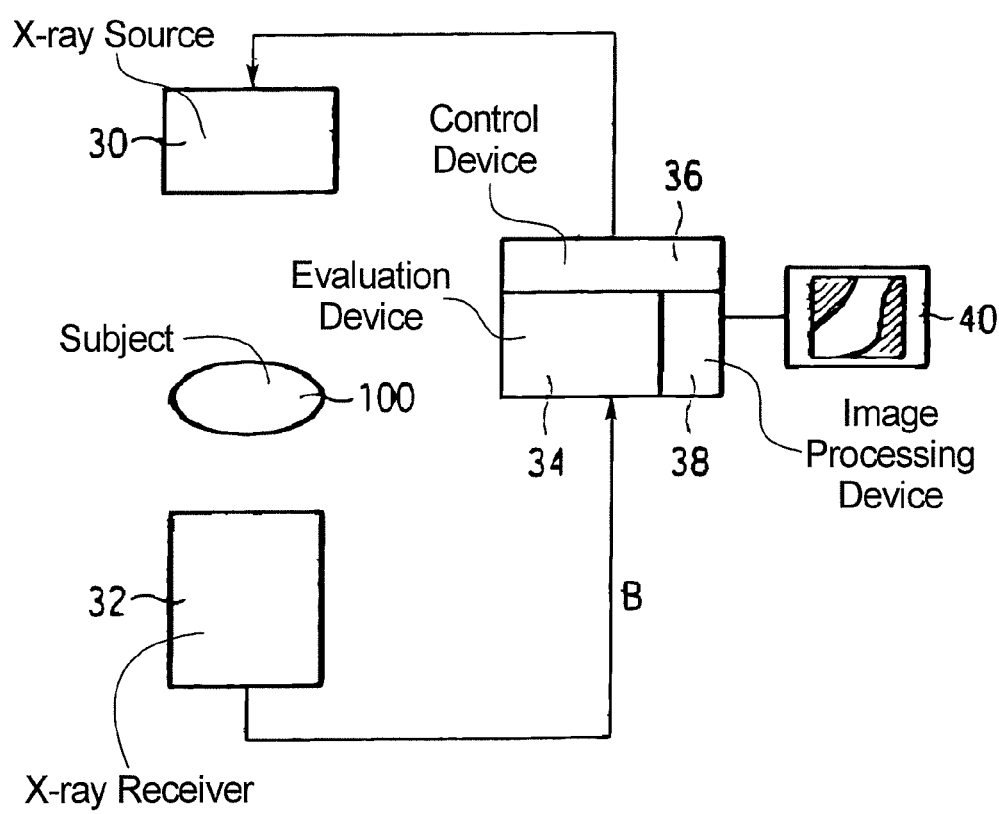
FIG. 12 is a block diagram of a device according to the invention.

As shown in FIG. 12, the apparatus according to the invention has an x-ray source 30 and an x-ray receiver 32 between which is located an examination subject 100. The image data B provided by the x-ray receiver 32 are evaluated in an evaluation device 34 with software that executes the method steps explained in the preceding. The x-ray source 30 is connected to a control device 36 in which the real value of an average intensity of a measurement field situated within the subject image region is compared with a stored desired value as explained above, and the control device 36 controls the x-ray dose emitted by the x-ray source 30 dependent on the comparison result.

Moreover, in an image processing device 38 the subject mask generated according to the methods explained in the preceding is used to identify the image regions of the x-ray image that are situated outside of the subject image region as virtual diaphragms by a uniform representation on a reproduction device 40 (a monitor in the example), as this is symbolically represented in FIG. 12 by hatching.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for generating an x-ray image of an examination subject, comprising the steps of:
   obtaining a first x-ray image having an image field that contains a subject image region that contains only an image of an examination subject, said first x-ray image being comprised of a plurality of image points each exhibiting a greyscale value within a predetermined greyscale value range that is dependent on an image reproduction medium;
   in a processor, digitally processing said first x-ray image to obtain an intermediate image encompassing said image field, said intermediate image being comprised of a plurality of image points equal to said plurality of image points of said first x-ray image, each exhibiting a grayscale value within said greyscale value range; and
   in said processor, identifying said subject image region in said intermediate image by associating with said subject image region all image points in said intermediate image exhibiting respective grayscale values within said grayscale value range; and
   making said intermediate image available at an output of the processor as a data file in a form for presentation at said image reproduction medium.

2. A method as claimed in claim 1 wherein said first x-ray image is obtained with an x-ray imaging system, and comprising, prior to obtaining said first x-ray image, obtaining a calibration image with said x-ray imaging system with no examination subject present, and deriving said intermediate image from said first x-ray image by generating a calibrated, second x-ray image by operating on said first said x-ray image with said calibration image, and deriving said intermediate image from said calibrated, second x-ray image.

3. A method as claimed in claim 2 comprising deriving said intermediate image from said calibrated, second x-ray image by edge filtering said calibrated, second x-ray image to identify edge regions therein, and deleting said edge regions from the edge filtered, calibrated, second x-ray image to obtain an edge-reduced x-ray image as said intermediate image.

4. A method as claimed in claim 1 comprising deriving said intermediate image from said first x-ray image by edge filtering said first x-ray image to identify edge regions therein, and deleting said edge regions from the edge filtered first x-ray image to obtain an edge-reduced x-ray image as said intermediate image.

5. A method as claimed in claim 1 comprising identifying said grayscale value range by generating a grayscale histogram representing a frequency of occurrence of the grayscale values in said intermediate image and assigning an artificial frequency of occurrence of zero to all grayscale values in said histogram having an actual frequency of occurrence that is below a predetermined threshold, said grayscale value range then comprising all grayscale values in said histogram having a non-zero frequency of occurrence.

6. A method as claimed in claim 1 wherein determining said image points exhibiting respective grayscale values in said grayscale value range includes generating a grayscale value histogram representing a frequency of occurrence of the grayscale values in said intermediate image, identifying a maximum grayscale value in said histogram, and determining whether said maximum grayscale value is less than or equal to a maximum possible grayscale value of a dynamic range available for said intermediate image.

7. A method as claimed in claim 6 wherein, if said maximum grayscale value in said histogram is less than said maximum possible grayscale value, executing a first search, in a first search interval of said histogram adjoining said maximum grayscale value, for a grayscale value M occurring in said first search interval with a maximum frequency of occurrence, and executing a second search, in a second search interval in said histogram adjoining and below said grayscale value, said second search proceeding through increasingly smaller grayscale values in said second search interval, for a first grayscale value in said second search interval that falls below a predetermined threshold, and identifying said first grayscale value found in said second search as an upper grayscale value of said grayscale value range.

8. A method as claimed in claim 7 wherein said upper grayscale value is a first upper grayscale value of a first grayscale value range for image points associated with a first subject image region, and comprising executing a further search in said grayscale value histogram, in a direction towards smaller grayscale values starting from said first upper grayscale value, for a first grayscale value in which said threshold is exceeded, and identifying said first grayscale value in said further search as a second upper grayscale value of a second grayscale value range for image points associated with a second subject image region.

9. A method as claimed in claim 6 wherein said maximum grayscale value in said histogram is equal to said maximum possible grayscale value, and executing a search, in a search interval in said grayscale value histogram having an upper limit formed by said maximum possible grayscale value, for a first grayscale value in said search interval having a frequency of occurrence below a predetermined threshold, and identifying said first grayscale value in said search as an upper grayscale of said grayscale value range.

10. A method as claimed in claim 9 wherein said upper grayscale value is a first upper grayscale value of a first grayscale value range for image points associated with a first subject image region, and comprising executing a further search in said grayscale value histogram, in a direction towards smaller grayscale values starting from said first upper grayscale value, for a first grayscale value in which said threshold is exceeded, and identifying said first grayscale value in said further search as a second upper grayscale value of a second grayscale value range for image points associated with a second subject image region.

11. A method as claimed in claim 1 comprising determining an average grayscale value of said subject image region, and using said average grayscale value to control a dose of x-ray radiation used to obtain a subsequent x-ray image, after said first x-ray image.

12. A method as claimed in claim 1 comprising displaying said subject image region of said first x-ray image in a display representation with regions outside of said subject image region displayed as a virtual diaphragm with a uniformed display appearance.

13. A method as claimed in claim 1 comprising displaying said first x-ray image in an image reproduction having image reproduction grayscale values, and determining said image reproduction grayscale values exclusively from the grayscale value range for said subject image region.

14. An apparatus for generating an x-ray image of an examination subject, comprising:
- an x-ray imaging system adapted to interact with an examination subject to obtain a first x-ray image having an image field that contains a subject image region that contains only an image of the examination subject, said first x-ray image being comprised of a plurality of image points each exhibiting a greyscale value within a predetermined greyscale value range that is dependent on an image reproduction medium;
- a digital processor configured to process said first x-ray image to obtain an intermediate image encompassing said image field, said intermediate image being comprised of a plurality of image points each exhibiting a grayscale value, and to identify said subject image region in said intermediate image by associating with said subject image region all image points in said intermediate image exhibiting respective grayscale values within said grayscale value range; and
- said digital processor being configured to make said intermediate image available at an output of the processor as a data file in a form for presentation at said image reproduction medium.

15. An apparatus as claimed in claim 14 wherein said digital processor is configured to determine an average grayscale value of said subject image region, and to use said average grayscale value to control a dose of x-ray radiation used by said x-ray imaging system to obtain a subsequent x-ray image, after said first x-ray image.

16. A digital image processor for generating an x-ray image of an examination subject, said digital image processor being supplied with a first x-ray image having an image field that contains, a subject image region that contains only an image of an examination subject, said first x-ray image being comprised of a plurality of image points each exhibiting a greyscale value within a predetermined greyscale value range that is dependent on an image reproduction medium, said digital image processor being programmed to digitally process said first x-ray image to obtain an intermediate image encompassing said image field, said intermediate image being comprised of a plurality of image points equal to said plurality of image points of said first x-ray image, each exhibiting a grayscale value, and to identify said subject image region in said intermediate image by associating with said subject image region all image points in said intermediate image exhibiting respective grayscale values within said grayscale value range, and make said intermediate image available at an output of the processor as a data file in a form for presentation at said image reproduction medium.

* * * * *